United States Patent [19]

Katzin

[11] Patent Number: 4,878,897
[45] Date of Patent: Nov. 7, 1989

[54] INJECTION SITE DEVICE HAVING A SAFETY SHIELD

[75] Inventor: Gerald H. Katzin, Raleigh, N.C.

[73] Assignee: Ideation Enterprises, Inc., Raleigh, N.C.

[21] Appl. No.: 935,286

[22] Filed: Nov. 26, 1986

Related U.S. Application Data

[63] Continuation-in-part of Ser. No. 863,577, May 15, 1986, abandoned.

[51] Int. Cl.$^4$ ............................................. A61M 5/14
[52] U.S. Cl. ..................................... 604/86; 604/192; 604/174; 128/DIG. 26
[58] Field of Search ................. 604/86, 174, 180, 192, 604/201, 244, 263, 283, 284; 128/DIG. 26

[56] References Cited

U.S. PATENT DOCUMENTS

| | | | |
|---|---|---|---|
| 2,402,306 | 6/1946 | Turkel | 604/174 |
| 3,186,411 | 6/1965 | Skidmore | 128/360 |
| 3,765,420 | 10/1973 | Felczak | 604/180 |
| 4,000,740 | 1/1977 | Mittleman | 604/86 |
| 4,048,995 | 9/1977 | Mittleman | 604/86 |
| 4,149,539 | 4/1979 | Cianci | 128/DIG. 26 |
| 4,161,177 | 7/1979 | Fuchs | 604/177 |
| 4,353,369 | 10/1982 | Muetterties et al. | 128/DIG. 26 |
| 4,417,890 | 11/1983 | Dennehey et al. | 604/283 |
| 4,559,042 | 12/1985 | Votel | 604/192 |
| 4,573,975 | 3/1986 | First et al. | 604/192 |
| 4,585,443 | 4/1986 | Kaufman | 604/174 |
| 4,627,842 | 12/1986 | Katz | 604/180 |
| 4,671,331 | 6/1987 | Pruden | 604/415 |
| 4,717,386 | 1/1988 | Simmons | 604/263 |
| 4,737,149 | 4/1988 | Gillian | 604/192 |
| 4,740,204 | 4/1988 | Masters et al. | 604/263 |
| 4,742,910 | 5/1988 | Staebler | 604/192 |
| 4,840,618 | 6/1989 | Marvel | 604/192 |

OTHER PUBLICATIONS

"Comp Gaurd", Comp Equipment Corporation, St. Paul, MN, Sales Pamphlet, 11/83.

Primary Examiner—Stephen C. Pellegrino
Assistant Examiner—Ralph Lewis
Attorney, Agent, or Firm—Richard E. Jenkins

[57] ABSTRACT

An injection site device having a shield extending outwardly from the tubular body thereof between the injection port and the outlet port in order to protect the fingers of the user when a needle is being introduced into the injection port of the injection site device.

7 Claims, 6 Drawing Sheets

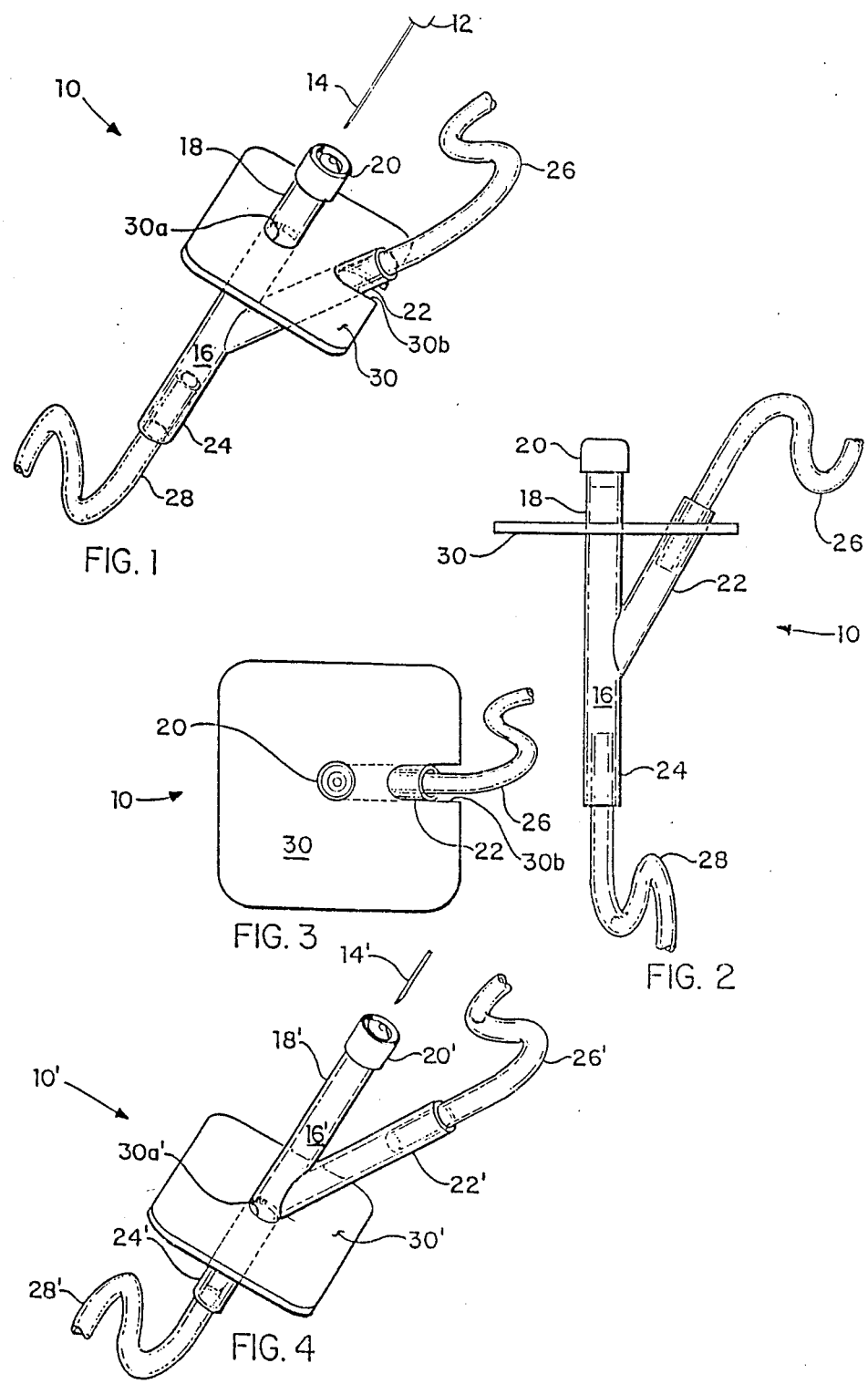

INJECTION SITE DEVICE HAVING A SAFETY SHIELD

RELATED APPLICATIONS

This application is a continuation-in-part application of Ser. No. 863,577 filed May 15, 1986 and entitled "Injection Site Device Having a Safety Shield," now abandoned.

TECHNICAL FIELD

The present invention relates to an injection site device of the type used with intravenous administration sets, dialysis equipment and the like for introducing and removing fluids from a flexible tube or the like. More particularly, the present invention concerns itself with an injection site device having a safety shield which is particularly helpful for protecting the hands of medical personnel from accidental puncture wounds while using the device.

BACKGROUND ART

The prior art contains a number of injection site devices of an improved nature but none are believed to be concerned with the problem of protecting the fingers of medical personnel when they are inserting a needle such as a hypodermic syringe needle into the injection port of an injection site device in order to introduce or to remove a fluid. At the time of the introduction or removal of the fluid by the needle, the fingers of the medical professional are in the greatest jeopardy of being punctured since the medical professional typically holds the injection site device in one hand and the needle in the other in order to insert the needle into the entry port of the injection site device. All too often this procedure results in the medical professional suffering a self-inflicted accidental prick or puncture wound.

References of interest include U.S. Pat. No. 4,559,042 which teaches providing a shield for the needle cover of a disposable hypodermic syringe. The shield is provided on the needle cover in order that the needle of the disposable hypodermic syringe may be covered after use without danger of a puncture wound to the fingers. Other references of possible interest include U.S. Pat. No. 4,121,585 which discloses an improved injection site device wherein the injection port is provided with two spaced-apart pierceable diaphragms to prevent backflow of parenteral solution into the syringe. U.S. Pat. No. 4,416,661 discloses an injection site having an improved entry port for introduction of the hypodermic syringe needle. U.S. Pat. No. 4,432,767 describes a tubing injection site guard which permits a syringe needle to be inserted into a tube without subsequent leakage and which protects the operator from a puncture wound injury while inserting the needle. Also, Falgro International Corporation of Miami Beach, Florida manufactures a removable cylindrical guard which is intended to be positioned around the neck of a medication bottle to facilitate safe withdrawal of the medication therein by hypodermic syringe.

DISCLOSURE OF THE INVENTION

In accordance with the present invention, applicant provides an injection site device of the type commonly used with an intravenous flow assembly, dialysis equipment and the like which is designed specifically to prevent injury to the fingers of a medical professional when a needle such as a hypodermic syringe needle is being inserted into the injection port of the injection site device. The invention provides for an injection site device which has a shield positioned in proximity to the injection port to protect the fingers of a medical professional when a needle is being inserted into the injection port of an injection site device. It is contemplated that the shield may be an integral part of the device or it may be removably secured thereto in the form of a retrofit device.

In a first embodiment of the invention, the shield is positioned immediately beneath the injection port at one end of the tubular body member of an injection site device in the form of a "Y" injection site and is constructed of a material such as plastic which is strong enough to resist piercing by a syringe needle. A variation of this embodiment contemplates that the shield will be positioned between the "Y" joint of a "Y" injection site device and the outlet port. Other embodiments of the invention contemplate use of the shield with an injection site device of the type having only an injection port and an outlet port, and in proximity to the injection port(s) of an injection site device of the type having a plurality of injection ports, inlet ports and/or outlet ports. Still other embodiments of the invention are contemplated, some of which are described hereafter.

It is accordingly one object of the present invention to provide an injection site device for use with an IV administration set, dialysis equipment and the like which provides a guard to protect the fingers of a medical professional user thereof from a puncture wound when a needle is inserted into the inlet port of the injection site device.

A further object of the present invention is to provide an injection site device whereby injection of an intravenous drug or removal of a fluid can be more easily accomplished by a medical professional.

Another object of the present invention is to provide an improved injection site device which serves to preserve the sterility of a hypodermic syringe and the contents of the syringe.

These and other objects of the present invention, as well as the attendant advantages thereof, will become more readily apparent when reference is made to the following description, taken in conjunction with the accompanying drawings.

BRIEF DESCRIPTION OF THE DRAWINGS

FIG. 1 is a perspective view of one embodiment of the inventive injection site device with a syringe needle about to be inserted into the injection port thereof;

FIG. 2 is a side elevation view of the inventive injection site device of FIG. 1;

FIG. 3 is a top plan view of the inventive injection site device of FIG. 1;

FIG. 4 is a perspective view of a variation of this embodiment of the invention;

BEST MODE FOR CARRYING OUT THE INVENTION

Figure 5:
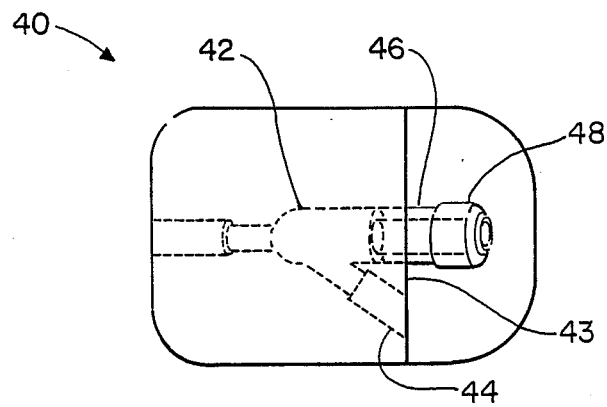
FIG. 5 is a top plan view of a second embodiment of the invention.

With reference to FIG. 1, the inventive injection site device is shown and generally designated 10. In a representative environment, device 10 would be utilized as a part of an IV administration set which typically includes a bottle or plastic bag containing parenteral solution with a flexible tube extending therefrom and being connected at its lower end to a patient. The device 10 is interposed along the flexible tubing so that a hypodermic syringe may be inserted therein to introduce a drug or the like into the solution being infused into the patient. A syringe 12 is shown in FIG. 1 with the needle 14 thereof about to be introduced into injection site device 10.

Injection site device 10 is of the "Y" shape type and comprises a tubular body portion 16 having an injection port 18 at the upper end thereof which typically includes a rubber diaphragm 20. An inlet port 22 extends outwardly from body portion 16 and is in fluid communication therewith. An outlet port 24 is located at the lower end of tubular body portion 16. Also, an upstream flexible tube 26 is connected to inlet port 22 at one end and to the container containing the solution being infused (not shown) at the other end. A downstream flexible tube 28 is connected at one end to outlet port 24 of injection site device 10 and at the other end to a patient (not shown). Positioned around injection port 18 of injection site device 10 is a shield 30 which may be constructed of plastic or any other suitable material which is sufficiently strong so as not to be capable of being punctured by needle 14 of syringe 12 if the needle is inadvertently brought into contact with shield 30 while attempting to insert it into rubber diaphragm 20.

With particular reference to FIGS. 1-3, shield 30 can be seen to have a generally centrally located aperture 30a through which injection port 18 extends and a peripherally positioned slot 30b through which inlet port 22 extends. As can best be seen in FIG. 2, shield 30 is slidably received by injection port 18 of tubular body portion 16 and slides down tubular body portion 16 until slot 30b comes into contact with and rests upon inlet port 22.

A variation of this embodiment of the invention is illustrated in FIG. 4 and comprises a shield 30' which is positioned below the juncture of inlet port 22' and injection port 18' and above outlet port 24'. Shield 30' has aperture 30a' positioned substantially in the middle portion thereof in order to be slidably received upon tubular body portion 16' of the injection site device.

It is also contemplated that shield 30 could have an upwardly extending conical shape in order to facilitate guiding syringe needle 14 into rubber diaphragm 20. A downturned skirt may be provided around at least a portion of the periphery of shield 30 in order to enable injection site device 10 to be more easily taped to a patient as needed. Moreover, shield 30 may be constructed of a rigid plastic or elastomeric material or, in the alternative, a flexible material to enable injection site device 10 to be compressed against the body of a patient. Shield 30 could also be constructed of a luminescent material to enable injection site device 10 to be more readily located in a darkened room.

Figure 6:
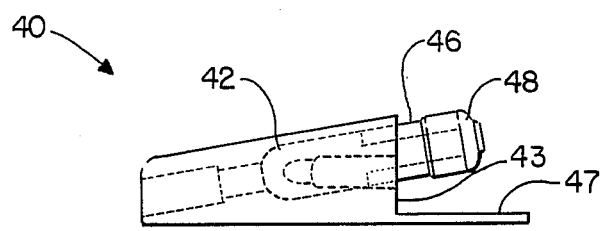
FIG. 6 is a side elevation view of the device of FIG. 5.
Figure 7:
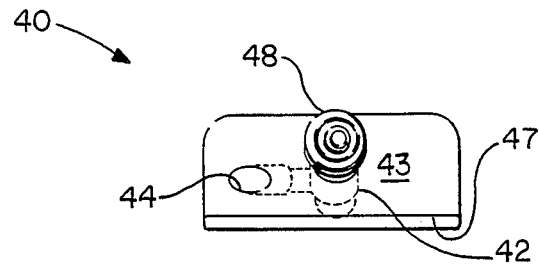
FIG. 7 is a front view of the device of FIG. 5.

Another embodiment of the invention is shown in FIGS. 5-7. In this case, the shield and the tubular body member are formed as an integral unit, generally designated 40. The "Y" channel 42 is integral with the body and shield 43 is formed out of the planar forward surface of the body containing the inlet port 44 and the injection port 46. In this manner, the thumb and forefinger of medical personnel introducing a needle into the injection site will be safely located as they will have their fingers located distally from the path of the needle should diaphragm 48 be missed. In addition, a skirt 47 may be provided which is an extension of the underside of the body member extending beneath the injection port 46 and diaphragm 48 so as to lie flat against the patient's skin when in use. It is intended that the skirt will be integral with the remainder of the body member. The skirt serves the function of protecting the patient from accidental puncture of the skin as can best be seen in FIGS. 5 and 6. The skirt also serves to provide a point with which the body member may be anchored to the skin of the patient with suitable means, such as adhesive tape and the like.

Figure 8:
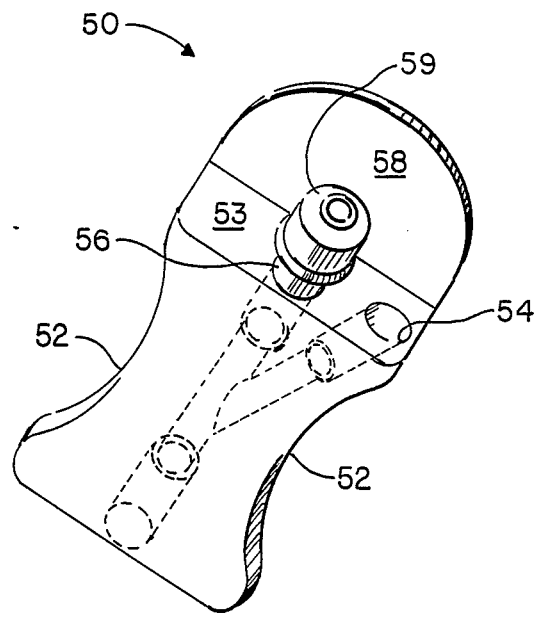
FIG. 8 is a perspective view of a third embodiment of the invention.
Figure 9:
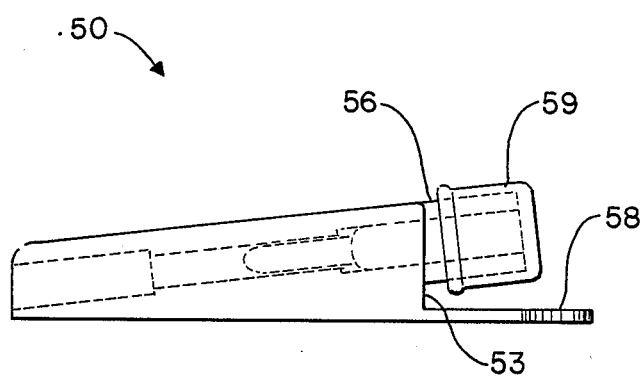
FIG. 9 is a side elevation view of the device of FIG. 8.

In an alternate embodiment, shown in FIGS. 8-9 and generally designated 50, the tubular body member includes a pair of medially located indented portions 52 positioned on opposite sides of the member for the fingers of the user to grip so that the fingers of the user are tucked safely behind the shield 53 formed by the forward vertical face of the body in which inlet port 54, injection port 56 and diaphragm 59 are located. Also, skirt 58 is provided to protect the patient from accidental wounds and to serve as means for taping the device to the patient.

Figure 10:
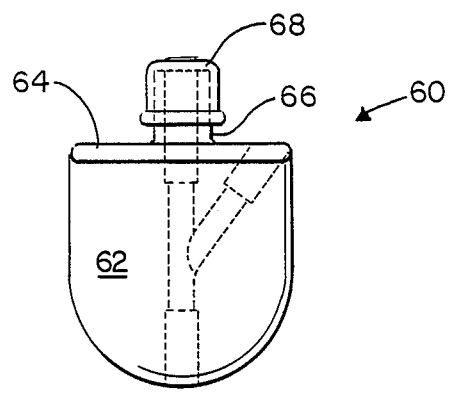
FIG. 10 is a side elevation view of a fourth embodiment of the invention.
Figure 11:
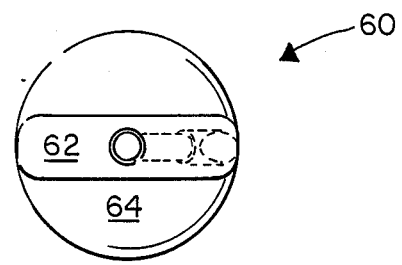
FIG. 11 is a bottom view of the device of FIG. 10.
Figure 12:
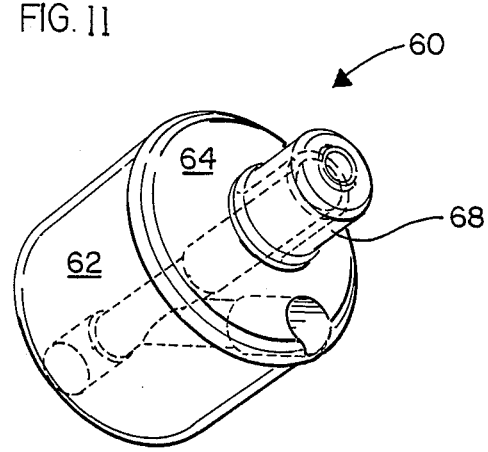
FIG. 12 is a perspective view of the device of FIG. 10.

FIGS. 10-12 depict still another embodiment of the invention which would not normally be in contact with the patient, generally designated 60, with gripping means 62 and a shield 64 around injection port 66 and diaphragm 68. Gripping means 62 typically comprises a cylindrical housing surrounding the bifurcated juncture of the injection site device as shown in FIGS. 10-12. It will be noted that the embodiments shown in FIGS. 5-12 include an integral "Y" channel and that the tubing for inlet and outlet of the IV fluid is inserted therein and is attached via suitable means such as adhesive. The injection port is also integral to the body member and may be formed during the molding process. In the two embodiments shown in FIGS. 5-9, the bore of the "Y" channel generally extends upwardly towards the injection port to facilitate insertion of a needle into the diaphragm of the injection port.

Figures 13, 14:
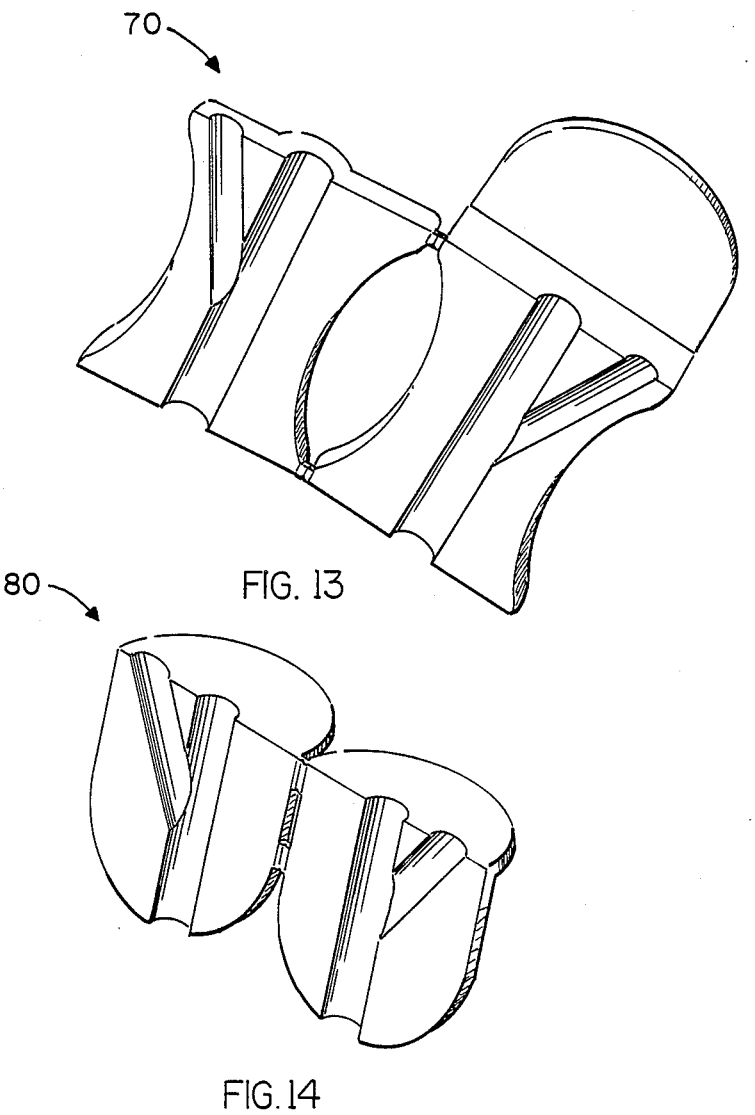
FIG. 13 is a perspective view of another embodiment of the device of FIG. 8.
FIG. 14 is a perspective view of another embodiment of the device of FIG. 10.

In another aspect of the invention, any of the embodiments illustrated in FIGS. 5-12 could be manufactured in a two-portion retrofit as represented in FIGS. 13 and 14. The two portions, generally designated 70 in FIG. 13 and 80 in FIG. 14, each form half of a "Y" channel into which the body member of a conventional "Y" injection site is inserted. The two halves may be hingedly connected, or completely separable, and when closed about the "Y" connector may be held together with glue, press fit, or other suitable means.

Figure 15:
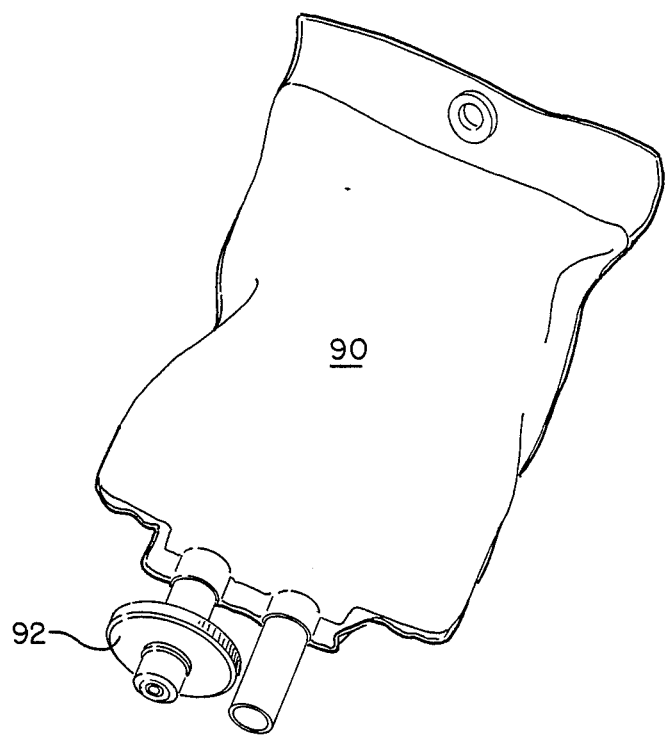
FIG. 15 is a perspective view of still another embodiment of the invention.

Still another contemplated embodiment of the instant invention provides a protective shield in proximity to the injection port of an injection site device of the type having only an injection port and an outlet port. FIG. 15 shows such an embodiment wherein the shield may be provided as a retrofit or as an integral portion of an injection site device attached to an IV bag 90. As with the other embodiments described, the shield 92 will serve to protect the fingers of medical personnel attempting to insert a needle into such an injection site attached to an IV bag.

Although not depicted, still another embodiment of the invention of the type having only an injection port and an outlet port and commonly used for administering multiple injections to a hospitalized patient, provides a protective shield in proximity to the injection port. Typically, a needle connected by a short tube to the outlet port thereof is inserted into a patient's vein for an extended period in order that the injection port will be readily accessible as needed from time to time to administer a drug or the like to the patient or to remove fluid without requiring repeated insertions of a hypodermic syringe needle into the patient. A further embodiment of the invention utilizes a protective shield proximate to the injection port or ports of an injection site device having a plurality of injection ports, inlet ports and/or outlet ports.

In operation, and with reference to FIGS. 1-3 for ease of explanation, a health care professional would grip tubular body portion 16 below shield 30 with one hand while utilizing the other to insert syringe needle 14 into the diaphragm 20 of injection site device 10. In this fashion, fingers of the hand supporting injection site device 10 are protected if syringe needle 14 should be misdirected and miss diaphragm 20 and extend downwardly toward the hand gripping injection site device 10. Thus, shield 30 prevents puncture wounds to the hand of a health care professional attempting to introduce a syringe needle into an injection site device in, for example, an IV administration set and the drug contamination and other problems which could result from puncture wound It will be understood that various details of the invention may be changed without departing from the scope of the invention. Furthermore, the foregoing description is for the purpose of illustration only, and not for the purpose of limitation—the invention being defined by the claims.

What is claimed is:

1. An injection site device suitable for facilitating the infusion of a drug and the like into a patient through the primary flow path of an IV administration system wherein the device comprises a bifurcated juncture of the generally "Y" shape type having in fluid communication, an injection port at a first end of a tubular body member, an inlet port adjacent the first end and extending outwardly from the body member, and an outlet port at the other end of a body member, the improvement which comprises grasping means extending generally outwardly from said tubular body member so that when the fingers of the user are applied to grasp the body member, they will be distally spaced from the injection port and out of the path of the needle should the user miss the injection port with the needle, said grasping means comprising a cylindrical housing surrounding the bifurcated juncture and extending radially outwardly from said tubular body member a distance sufficient to fully remove the fingers of a user from the area immediately surrounding the injection port.

2. An injection site device suitable for facilitating the infusion of a drug and the like into a patient through the primary flow path of an IV administration system wherein the device comprises a bifurcated juncture of the generally "Y" shape type having in fluid communication, an injection port at a first end of a tubular body member, an inlet port adjacent the first end and extending outwardly from the body member, and an outlet port at the other end of a body member, the improvement which comprises: a finger protecting shield means extending generally radially outwardly from the tubular body member and positioned between the injection port and the outlet port of the device for protecting a user's fingers from needle puncture when the injection site device is held in one hand beneath the shield means and the other hand is used to insert a needle into the injection port, said shield means extending radially outwardly from said tubular body member a distance sufficient to fully shield the fingers of a user from said needle, said shield means further including a non-foldable skirt connected to said body member at an angle to said shield means and being adapted to lie flat against the skin of a patient for increased comfort and to further protect the patient from accidental puncture by the needle.

3. An injection site device according to claim 2 wherein said skirt is adapted for the application of adhesive tape thereon to fix the location of the body member on the skin of the patient.

4. An injection site device suitable for facilitating the infusion of a drug and the like into a patient through the primary flow path of an IV administration system wherein the device comprises:
   a housing formed out of a first portion and a second portion and adapted to be positioned about an existing bifurcated channel juncture;
   a bifurcated channel juncture of the generally "Y" shape type within and extending through said housing of the type having in fluid communication first and second inlet ports at one end of the housing;
   an outlet port at the opposite end of said housing, said first and second inlet ports being independent of one another and said second inlet port and said outlet port being adapted to receive the end of a catheter tubing; and
   shield means proximate said first and second inlet ports for protecting a user's fingers from needle puncture when the injection site device is held in one hand beneath the shield means and the other hand is used to insert a needle into the first inlet port, said shield means extending radially outwardly from said first inlet port a distance sufficient to fully shield the fingers of a user from said needle.

5. An injection site device according to claim 4 wherein said first and second portions are adapted to be hingedly connected about an existing bifurcated channel juncture.

6. An injection site device according to claim 4 wherein said first and second portions are adapted to be secured together about an existing bifurcated channel juncture.

7. An injection site device suitable for facilitating the infusion of a drug and the like into a patient through the primary flow path of an IV administration system wherein the device comprises a bifurcated juncture of the generally "Y" shape type having in fluid communication, an injection port at a first end of a tubular body member, an inlet port adjacent the first end and extending outwardly from the body member, and an outlet port at the other end of a body member, the improvement which comprises: a finger protecting shield means extending generally radially outwardly from the tubular body member and positioned between the injection port and the outlet port of the device for protecting a user's fingers from needle puncture when the injection site device is held in one hand beneath the shield means and the other hand is used to insert a needle into the injection port, said shield means extending radially outwardly from said tubular body member a distance sufficient to fully shield the fingers of a user from said needle, and wherein a portion of the shield means is substantially flat whereby the tubular body member and said shield means may be positioned flatly on the skin of a patient to achieve increased patient comfort.

* * * * *